United States Patent [19]

Ito

[11] 4,264,153
[45] Apr. 28, 1981

[54] EYE FUNDUS INSPECTION DEVICE CAPABLE OF HIGH SPEED FOCUSING

[75] Inventor: Yuji Ito, Chigasaki, Japan

[73] Assignee: Canon Kabushiki Kaisha, Tokyo, Japan

[21] Appl. No.: 922,271

[22] Filed: Jul. 6, 1978

[30] Foreign Application Priority Data

Jul. 11, 1977 [JP] Japan .................................. 52-82734

[51] Int. Cl.³ .......................... A61B 3/14; A61B 3/10; G03B 29/00
[52] U.S. Cl. ........................................ 351/7; 351/13; 351/16; 354/62
[58] Field of Search ........................... 351/6, 7, 13, 16; 354/62

[56] References Cited

U.S. PATENT DOCUMENTS

| 2,940,371 | 6/1960 | Thurow | 354/62 |
| 3,016,000 | 1/1962 | Noyori | 354/62 |
| 3,259,039 | 7/1966 | Okajima | 354/62 X |
| 3,925,793 | 12/1975 | Matsumura et al. | 351/7 X |

Primary Examiner—John K. Corbin
Assistant Examiner—Rodney B. Bovernick
Attorney, Agent, or Firm—Toren, McGeady and Stanger

[57] ABSTRACT

The disclosed eye examination device focuses on the fundus of an eye. A transparent plate with a black line or a plate with a slit is illuminated and the image of the black line or the slit projected on the eye fundus through an objective lens. A bi-prism with a split plane is arranged so that the split plane is always optically conjugate with the transparent or slit plate relative to the eye fundus. When observed through the bi-prism, the image of the black line or the slit forms one line when the eye fundus is exactly in focus, while the image is separated when the eye fundus is out of focus.

10 Claims, 11 Drawing Figures

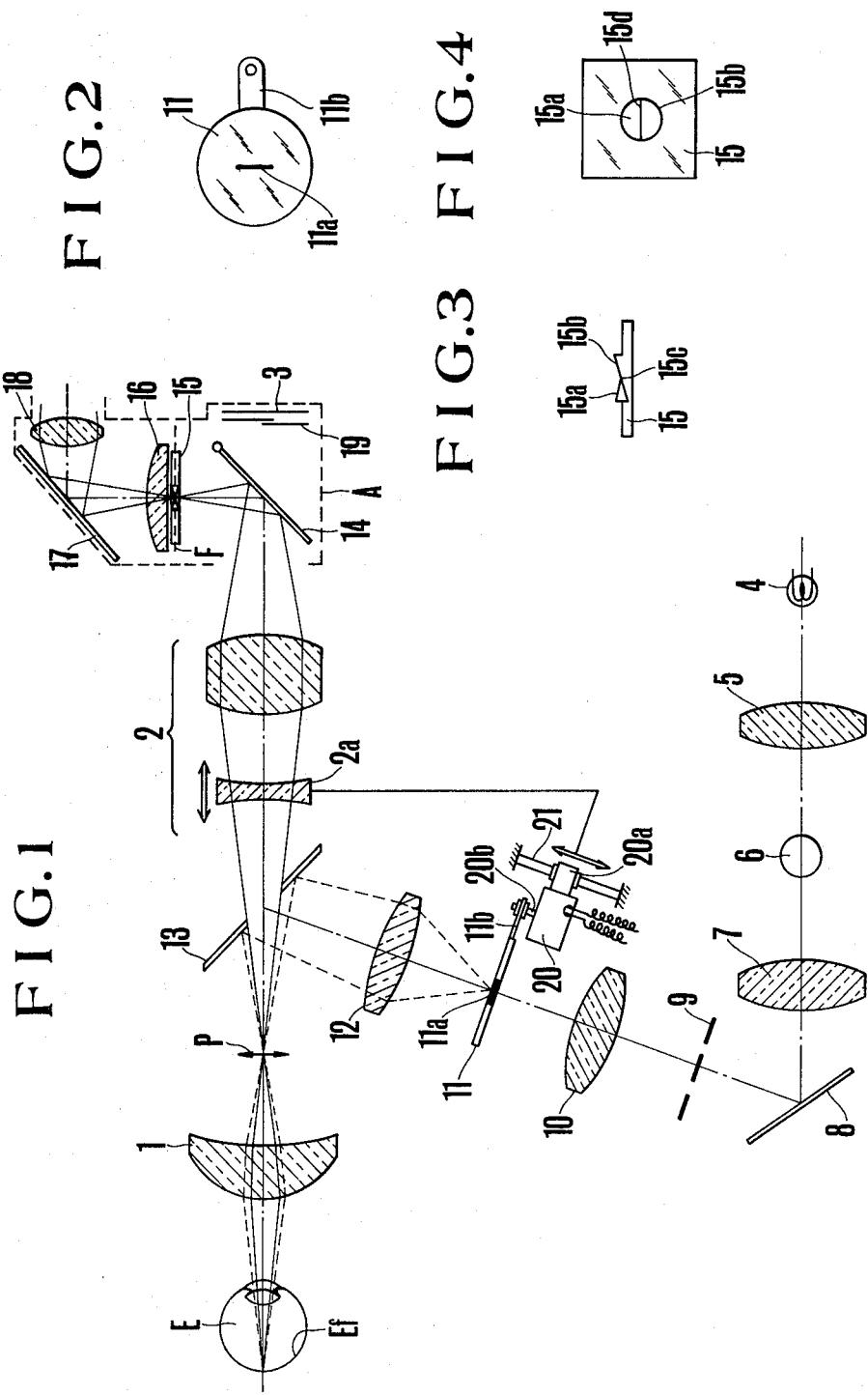

EYE FUNDUS INSPECTION DEVICE CAPABLE OF HIGH SPEED FOCUSING

BACKGROUND OF THE INVENTION

The present invention relates to an eye examining instrument, particularly one for exactly focusing on the retina of a human eye.

Generally, to focus an eye fundus camera, the eye fundus is illuminated, the diopter of the observer is matched and a cross line on a focusing screen, the clear image of the eye fundus is obtained. However, the fundus of the human eye contains few focusing targets. When the veins in the fundus are used as a target, the optical axis of the camera has to be deflected to bring the veins into the visual field and then the camera returned to its initial visual field. This is troublesome and requires substantial experience.

In order to eliminate these difficulties, U.S. Pat. No. 3,016,000 proposes a system in which the image of a small cross line is projected on the eye fundus and served directly or through a half-transparent mirror. The system is then focused to obtain a clear image of the cross line. However, the individual differences play an important role in the judgement of the clearness of the image.

On the other hand, U.S. Pat. No. 3,925,793 proposes an eye fundus camera focus which eliminates individual differences. However, this camera focuses by making a focusing target is out of the paraxis and the focusing accuracy is unavoidably decreased.

SUMMARY OF THE INVENTION

An object of the present invention is to offer a device by means of which the eye fundus focus can be judged objectively.

A second object of the present invention is to offer a device which focuses by making use of the paraxial beam.

Still another object of the present invention is to provide a device which enables quick and accurate focusing.

Yet another object of the present invention is to offer a device whose assembly and adjustment are easy.

In order to achieve the above objects, the image of the focusing target is projected on the fundus of the eye to be inspected through the projection system and the image of the target reflected on the eye fundus is formed on optical refracting means arranged in the observation system through the image forming optical system, while the focusing target cooperates with the optical refracting means.

BRIEF EXPLANATION OF THE DRAWINGS

FIG. 1 shows an embodiment of the present invention in section.

FIG. 2 shows the index plate in plane view.

FIG. 3 shows the bi-prism plate in section.

FIG. 4 shows the bi-prism plate in plane view.

DESCRIPTION OF THE PREFERRED EMBODIMENT

Figures 5, 6, 7:
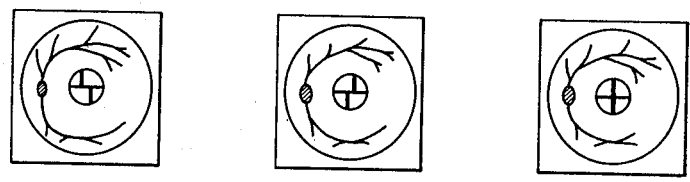
FIGS. 5, 6 and 7 respectively show a visual field in the finder.

In FIG. 1, an eye E to be inspected includes an eye fundus EF. An objective lens 1 and a convergent lens constitute an image forming optical system of the eye examining instrument. The objective lens 1 forms an image plane P for the eye fundus of an ideal eye. The above mentioned convergent lens 2 serves to reform the image of the eye fundus image of the image plane P on a film 3. A standard image forming plane F receives the image on the image plane P through the convergent lens 2 and a pivotable mirror 14. A focusing lens 2a is movable along the optical axis so as to obtain focusing of the image forming optical system.

The instrument is also composed of an observation lane 4, condenser lenses 5 and 7, an electronic discharge tube 6, an optical path deflecting mirror 8, and a slit plate 9 having a ring-shaped opening. The light emitted from the lamp 4 and that from the tube 6 are condensed on the slit plate 9. Two relay lenses 10 and 12 form the image of the split plate 9 on a mirror 13 having an aperture and positioned obliquely to the optical axis. The above mentioned elements 4-10, 12 and 13 and the objective lens 1 constitute an illumination system.

As shown in FIG. 2, a transparent index plate with a line-shaped index 11a is connected with an arm 11b, which is secured on a rotary shaft 20b of a rotary-solenoid 20. When a current is supplied to the rotary-solenoid 20 to rotate the shaft 20b the index plate 11 is moved out of the optical path between lenses 10 and 12. A guide rod 21 secured on a housing not shown in the drawing carries a sliding portion 20a connected with the solenoid 20 so that the index plate is movable along the optical axis of the relay lenses 10 and 12. Further, the index plate 11 is operatively coupled to the focusing lens 2a in such a manner that the relation between the eye fundus Ef and the standard image forming plate F with reference to the objective lens 1 and the convergent lens 2 is always kept equal to the relation between the eye fundus Ef and the index 11a with reference to the mirror 13, the objective lens 1 and the release lens 12. In consequence, when the eye fundus is conjugate to the standard image forming plane, the eye fundus is also conjugate to the index.

A bi-prism plate 15 structured as shown in section in FIG. 3 and in the plan view in FIG. 4, is composed of two planes oppositely inclined in the middle of a transparent plate. The intersecting point 15c of the edges of the two inclined planes corresponds to the standard image plane F with the boundary 15d between the two incline planes is normal to the index line 11a. Member 16 is a field lens, 17 is an optical path deflecting mirror, 18 is an eye piece lens and 19 is a shutter curtain.

When the objective lens 1 is directed toward the eye to be inspected and the lamp 4 is lit, the light beam emitted from the lamp 4 is once condensed upon the speed light tube 6 by means of the condenser lens 5, is made to diverge and then condensed again on the slit plate 9 by means of the condenser lens 7, after having been reflected by means of the mirror 8. The light beam passing through the opening in the slit plate 9 is converted into a parallel beam by means of the relay lens 10 to illuminate the index plate 11 and then condensed on the mirror 13 by means of the second relay lens 12, reflected by the mirror 13 and then condensed in the neighborhood of the iris of the eye E to be inspected by means of the objective lens 1, so as to illuminate the eye fundus Ef. Then the object light beam from the eye fundus Ef emerges from the eye E to be inspected so that the lens 1 forms an image on the image plane P, which passes through the converging lens 2 and is reflected by the pivoting mirror 14 so the image is again formed on the image plane F. Thus, it is possible for the observer looking through the eye piece 18 to observe the image of the eye fundus formed on the image plane F through the mirror 17 and the field lens 16.

On the other hand, every human eye has a different diopter and therefore the light beam emitted from the eye E to be inspected does not always from an image on the image plane P but a little before or behind the plane P. Thus it is necessary for the observer to adjust the position of the focusing lens 2a so the image of the eye fundus not exactly formed on the image plane P is exactly formed on the standard image plane F. Hence it is difficult to decide the standard point for moving the focusing lens 2a, which is the background of the present invention.

The index plate 11 is illuminated by the light beam emitted from the lamp 4 so that the image of the index 11a is formed on the image plane P by the relay lens 12 and the mirror 13. The image of the index is now formed on the eye fundus Ef by the objective lens 1. The image of the index is then formed on the standard image forming plane F through the objective lens 1, the convergent lens 2 and the mirror 14 in the same manner as the image of the eye fundus.

When at this time, the image of the index is exactly formed on the standard image forming plane F, the light beam forming the image of the index can be observed by the observer through the prism plate 15, without being reflected by the incline planes 15a and 15b. FIG. 7 shows the resulting visual field in the view finder. Here the index image assumes the original shape. However, when the image of the index is formed before or behind the standard image forming plane F, the light beam incident on the inclined plane 15a is refracted along one direction and the light beam incident on the inclined plane 15b is refracted along another direction. Both light beams then reach the eye piece lens so that the image of the index is separated by the boundary line 15d, as is shown in FIGS. 5 and 6, where the upper image part does not correspond to the lower part. The correlative position of the upper position to the lower position when the image is formed before the prism plate 15 is reversed to that when the image is formed behind the prism plate.

Consequently, when the observer adjusts the focusing lens 2a so that the upper portion of the image of the index is aligned with the lower portion, the eye fundus Ef is conjugate with the film with reference to the objective lens 1 and the convergent lens 2. The solenoid 20 is then actuated by means of the release operation so as to withdraw the index plate 11 out of the optical path, raise the mirror 14, actuate the speed light tube 6, open the shutter 19 and expose the film 3 to the light from the object to be photographed.

Instead of moving the focusing lens 2a, it is sufficient to alter the distance between the image forming lens 2 and the mirror 14. For that purpose, according to another embodiment of the invention, the unit A is operatively engaged with the index plate 11.

Figure 8:
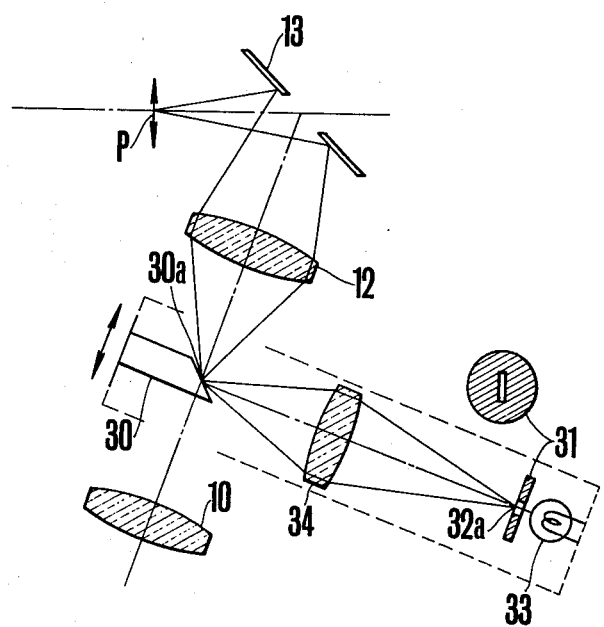
FIG. 8 shows an important part of a variation of the embodiment shown in FIG. 1 in section.

Although in the above mentioned embodiment the observation lamp is used as light source, an index illumination light source can be provided separately. FIG. 8 shows the important part of a variation of the embodiment shown in FIG. 1. In FIG. 8, a reflecting bar 30 has an inclined mirror plane 30a which intercepts the optical axis of the relay lenses 10 and 12 at the same position as the index 11a in FIG. 1. A light shading plate 31 is provided with a line-shaped index slit 32a. An illumination lamp 33 lights the slit 32. A positive lens, 34 forms the image of the slit 32a on the mirror plane 30a. Namely, the image of the index 32a is formed on the image plane P in the same way as in FIG. 1. The members 30-34 form one unit operatively engaged with the focus adjusting means so as to be moved along the optical axis of the relay lens. Further, the reflecting bar 30 is withdrawn from the optical path in response to the release operation immediately before the discharge of the electronic flash.

Figure 9:
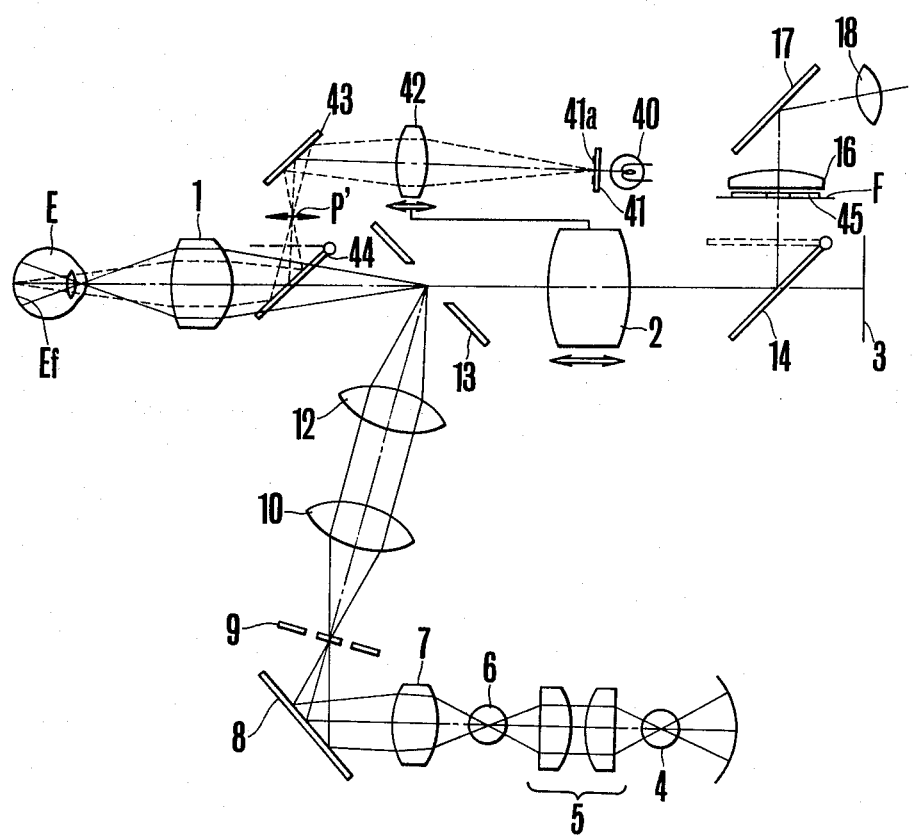
FIG. 9 shows another embodiment in section.
Figure 10:
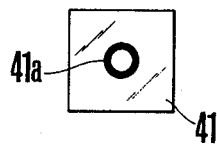
FIG. 10 shows the index plate in plane view.

FIG. 9 shows another embodiment. Here, members alike to those in FIG. 1 have the same reference characters. An index illumination lamp 40 lights an index plate having an index 41a on a transparent plate as is shown in FIG. 10. Member 42 is a convergent lens, 43 is an optical deflecting mirror and 44 is a semi-transparent mirror which can be set at a slant or withdrawn. A plane P' receives the image of the objective lens 1 to be formed with the light beam reflected with the semi-transparent mirror 44. The plane P' corresponds to P in FIG. 1. The convergent lens 2 is movable for focus adjustment, while the convergent lens 42 is operatively engaged with the convergent lens 2, maintains a given relation with the lens 2, such that the relation between the eye fundus and the standard image forming plane is kept equal to that between the eye fundus and the index with reference to the respective optical members.

Figure 11:
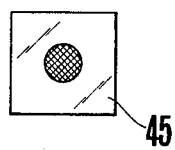
FIG. 11 shows the micro-prism plate in plane view.

A prism plate 45 having micro-prism array in the middle as is shown in plane view in FIG. 11 is aligned with the standard image forming plane F and can be dismounted from without for observation of the whole visual field.

When the lamp 40 of the above mentioned device is lit so as to illuminate the index plate 41, the image of the index 41a is formed on fundus Ef through the convergent lens 42, the mirror 43, the semi-transparent mirror 44 and the objective lens 1, is reflected there, passes through the semi-transparent mirror 44 and the convergent lens 2 and is reflected by mirror 14 in such a manner that the image of the index is formed on the standard image forming plane F or in the neighborhood thereof. This image can be observed through the field lens 16, the mirror 17 and the eye piece lens 18 as a focused or defocused image.

At this time, the image of the index passes through the micro-prism portion of the prism plate 45. Here, if the image is focused the image of the index 41a can be observed in the visual field of the view finder as the index 41a. If the image is out of focus the image of the index 41a observed in the view finder is deformed. By moving the convergent lens 2 to rectify the image of the index in the visual field, the eye fundus becomes conjugate with the standard image forming plane F to the objective lens 1, the convergent lens 2 and the mirror 14, on a proper focus is obtained.

Further, either the one of the two inclined planes of the split bi-prism can be made parallel to the base plane alternatively, in order to realize the Duo focus principle a cylindrical lens can be provided instead of prisms so that the image of the index is inclined to the generation line.

In accordance with the above mentioned embodiments, a paraxial beam can be used as the focusing beam for obtaining highly accurate focusing.

What is claimed is:

1. An eye examining instrument, comprising:
   an eye inspecting system able to focus on an eye fundus, including:
   objective means for facing the eye to be inspected and for causing light from the fundus of the eye to converge,
   a basic lens group behind said objective means for forming an image,
   an observing system optically coupled to said basic lens group for observing an image, and
   illuminating means for illuminating the eye fundus;
   said eye inspecting system forming an optical path;
   a mark projecting system for projecting the image of a mark on the fundus of the eye to be inspected, including:
   a mark,
   mark holding means for holding the mark,
   a light source for illuminating said mark,
   image transmitting means for transmitting the image of said mark,
   reflecting means in the optical path of said eye inspecting system for reflecting light from the image transmitting means,
   adjusting means simultaneously focusing said eye inspection system and adjusting said eye inspection system for adjusting the axial position of the image of said mark; and
   light deflecting means in said observing system for having the image of the mark formed thereon with the light from the basic lens group and for refracting a portion of the light so as to distort the image of the mark when the image of the mark is out of focus on the deflecting means and to maintain the image of the mark when the image of the mark is in focus on the deflecting means.

2. An eye examining instrument in accordance with claim 1, wherein the observing system has a swingable mirror, the eye inspecting system having photosensitive means at the image end of said basic lens system, the beam deflecting means being conjugate with said photosensitive means with reference to said swingable mirror.

3. An eye examining instrument in accordance with claim 2, wherein the deflecting means includes a bi-prism.

4. An eye examining instrument in accordance with claim 2, wherein the deflecting means includes an array of micro-prisms.

5. An eye examining instrument in accordance with claim 1, wherein the illuminating means includes the light source, a light transmitting means, the image transmitting means, the reflecting means and the objective optical means, and the mark being arranged between the light transmitting means and the image transmitting means.

6. An eye examining instrument in accordance with claim 1, wherein the illuminating means includes at least one light source, a light transmitting means, the reflecting means and the objective optical means, the image transmitting means including a second dismountable reflecting means in the optical path and the above reflecting means being arranged between the light source and the second reflecting means.

7. An eye examining instrument in accordance with claim 1, wherein the illuminating means includes at least one light source, a light transmitting means and an illuminating mirror arranged between the objective optical means and the basic lens group and the reflecting means being adjacent to the illuminating mirror.

8. An eye examining instrument, comprising:
   objective means for facing an eye to be examined,
   illuminating means for illuminating the fundus of the eye to be examined along a light path passing through said objective means,
   viewing means behind said objective means for receiving light from the fundus through said objective means so that an image of the fundus can be viewed, said viewing means including a focusing screen,
   variable focusing means between said objective means and said viewing means for focusing the light from the fundus upon the viewing means,
   mark imaging means for injecting an image of a mark into the light path passing through the objective means,
   said focusing screen including means for maintaining the image of the mark when the mark is in focus on the screen and for distorting the image of the mark at other times
   said mark imaging means being coupled to said focusing means for moving the image so as to focus the image on the fundus when the mark is focused upon said focusing screen.

9. An instrument as in claim 8, wherein:
   said focusing screen is located so that a focused image and an unfocused image of the mark may be formed thereon.

10. An eye examining instrument, comprising:
    an eye inspecting system able to focus on an eye fundus, including:
    objective means for facing the eye to be inspected and for causing light from the fundus of the eye to converge,
    a basic lens group behind said objective means for forming an image,
    an observing system optically coupled to said basic lens group from observing an image, and
    illuminating means for illuminating the eye fundus;
    said eye inspecting system forming an optical path;
    a mark projecting system for projecting an image of a mark on the fundus of the eye to be inspected, including:
    a mark,
    mark holding means for holding the mark,
    a light source for illuminating said mark,
    image transmitting means for transmitting the image of said mark,
    reflecting means in the optical path of said eye inspecting system for reflecting light from the image transmitting means,
    adjusting means for simultaneously focusing said eye inspection system and adjusting the axial position of the image of said mark; and
    optical means in said observing system located so that a focused image and an unfocused image of a mark can be formed thereon, and having means for distorting the image of the mark when unfocused while maintaining the image of the mark when the image of the mark is focused on said distorting means.

* * * * *